(12) United States Patent
Kelkar et al.

(10) Patent No.: US 6,380,426 B1
(45) Date of Patent: Apr. 30, 2002

(54) PROCESS FOR THE PREPARATION OF A CARBOXYLIC ACID

(75) Inventors: Ashutosh A Kelkar; Sunil S Tonde; Raghunath V Chaudhari, all of Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/962,601

(22) Filed: Sep. 26, 2001

(51) Int. Cl.$^7$ .......................... C07C 51/12; C07C 51/16
(52) U.S. Cl. .................. 562/519; 562/519; 562/538
(58) Field of Search ................................. 562/519, 538

(56) References Cited

U.S. PATENT DOCUMENTS 4,100,359 A * 7/1978 Schmerling et al.
5,919,978 A * 7/1999 Packett et al.

FOREIGN PATENT DOCUMENTS

EP 0133331 * 7/1984

* cited by examiner

Primary Examiner—Gary Geist
Assistant Examiner—Farhad Forohar
(74) Attorney, Agent, or Firm—Nixon & Vanderhye P.C.

(57) ABSTRACT

The present invention relates to a process for the preparation of a carboxylic acid by carbonylating the corresponding alcohol in carbon monoxide atmosphere and in the presence of water, a solvent, a palladium catalyst and a promoter system consisting of an organic or inorganic halide and an organic sulphonic acid, at a temperature in the range of 50–250° C., at a pressure in the range of 50–2000 psig for 1 to 10 hours, the concentration of the catalyst being one mole of catalyst per every 50–50000 moles of the alcohol, the amount of the organic or inorganic halide being in the range of 5–500 moles per mole of the catalyst, and the amount of the organic sulphonic acid being in the range of 5–500 moles per mole of the catalyst, collecting the resulting product.

15 Claims, No Drawings

PROCESS FOR THE PREPARATION OF A CARBOXYLIC ACID

FIELD OF THE INVENTION

The present invention relates to a process for the preparation of a carboxylic acid. Particularly, the present invention relates to a process for the preparation of a carboxylic acid by the reaction of an alcohol with carbon monoxide in the presence of a palladium compound as catalyst, an organic or an inorganic halide and an organic sulphonic acid as promoter, water and a solvent under mild conditions.

BACKGROUND OF THE INVENTION

Acetic acid has been produced industrially on a large scale by methanol carbonylation by the well known Monsanto and Cativa™ processes. U.S. Pat. No. 3,816,490, European Patents EP 728726A1 and EP 752406A1 disclose the use of rhodium or iridium as catalyst to produce acetic acid using methanol and carbon monoxide in the presence of iodide promoters and water. The disadvantage of these processes is the high costs and limited availability of the catalyst. The use of nickel in the presence of iodides has been reported for the carbonylation of methanol to acetic acid [U.S. Pat. No. 4,902,569 and J. Catal. (156), 290, (1995)]. However these processes use drastic conditions.

Palladium and platinum catalysts carbonylation of methyl iodide to acetic acid with quaternary iodide promoter is disclosed in J. Chem. Soc. Chem. Commun. 179–180 (1999). However the activity level is low (Turn Over Number TON=110), and methyl iodide is used as starting material. European Patent EP 0133331 discloses the palladium catalysed carbonylation of methanol to acetic acid in the presence of metal iodide, methyl iodide and sulfolane or sulfoxide. However, in this process sulfolane or sulfoxide are essential components.

As can be seen, the prior art processes suffer from several disadvantages such as the use of expensive starting materials resulting in higher cost of production; low activity; or require extreme operating conditions thereby rendering the process expensive. It is therefore important to develop a process for the preparation of a carboxylic acid that overcomes the drawbacks enumerated above.

OBJECTS OF THE INVENTION

The main object of the present invention is to provide a process for the preparation of a carboxylic acid that overcomes the twin drawbacks of low activity and drastic reaction conditions.

It is another object of the invention to provide a process for the preparation of a carboxylic acid that operates at milder reaction conditions.

It is a further object of the invention to provide a process for the preparation of a carboxylic acid such as acetic acid using metal halides and organic sulphonic acid as promoters.

It is yet another object of the invention to provide a process for the preparation of a carboxylic acid that is efficient and less expensive.

SUMMARY OF THE INVENTION

These and other objects of the invention are achieved by providing a palladium catalysed process for the carbonylation of an alcohol to the corresponding carboxylic acid in the presence of halide and organic sulphonic acid promoters, water and a solvent at milder reaction conditions.

Accordingly, the present invention provides a process for the preparation of a carboxylic acid comprising carbonylating the corresponding alcohol in carbon monoxide atmosphere and in the presence of water, a solvent, a palladium catalyst and a promoter system consisting of an organic or inorganic halide and an organic sulphonic acid, at a temperature in the range of 50–250° C., at a pressure in the range of 50–2000 psig for 1 to 10 hours, the concentration of the catalyst being one mole of catalyst per every 50–50000 moles of the alcohol, the amount of the organic or inorganic halide being in the range of 5–500 moles per mole of the catalyst, and the amount of the organic sulphonic acid being in the range of 5–500 moles per mole of the catalyst, collecting the resulting product.

In one embodiment of the invention, the alcohol used is ROH wherein R is an alkyl group having 1 to 5 carbon atoms.

In another embodiment of the invention, the catalyst used comprises palladium (II) or palladium (0) compound selected from the group consisting of palladium chloride, palladium bromide, palladium iodide and palladium acetate; or a metal complex of palladium selected from the group consisting of bis(triphenylphosphino)dichloropalladium (II), bis(triphenylphosphino)bibromopalladium (II), bis(triparatolylphosphino)dichloropalladium (II), bis(triparatolylphosphino)bibromopalladium (II), tetrakis(triphenylphosphino) dichloropalladium (0) and tetrakis(triphenylphosphino)dibromopalladium (0).

In a further embodiment of the invention, the organic halide used is of the formula RX wherein R is an alkyl group having 1 to 5 carbon atoms and X is a halogen selected from Cl, Br, and I.

In another embodiment of the invention, the inorganic halide used is of the formula MX wherein M is hydrogen or an alkali metal selected from the group consisting of Li, Na and K, and X is a halogen selected from Cl, Br and I.

In another embodiment of the invention, the organic sulphonic acid used is selected from the group consisting of benzene sulphonic acid, paratolyl sulphonic acid, methane sulphonic acid, and trifluoromethane sulphonic acid.

In a further embodiment of the invention, the solvent used comprises a ketone selected from the group consisting of acetone, diethyl ketone and acetophenone; or a cyclic ether selected from tetrahydrofuran and dioxan; or a nitrile selected from acetonitrile and benzonitrile; or an organic solvent selected from toluene and benzene.

In another embodiment of the invention, the concentration of the catalyst is one mole of catalyst for every 100–5000 moles of the alcohol, preferably one mole of catalyst for every 150–1000 moles of the alcohol.

In another embodiment of the invention, the amount of organic or inorganic halide promoter used is in the range of 25 to 150 moles per mole of catalyst.

In yet another embodiment of the invention, the amount of the organic sulphonic acid used is in the range of 50–150 moles per mole of catalyst.

In a further embodiment of the invention, the amount of water is in the range of 1 to 30%(v/v) of the total reaction mixture, preferably 3–25%.

In another embodiment of the invention, the pressure of the carbon monoxide used is in the range of 200–1000 psig.

In a further embodiment of the invention, the temperature of the reaction mixture is in the range of 70–200° C.

DETAILED DESCRIPTION OF THE INVENTION

The invention will now be described with reference to the following examples, which are illustrative and should not be construed as limiting the scope of the invention in any manner.

EXAMPLE 1

A 50 ml autoclave was charged with the following:

| | |
|---|---|
| Methanol | 0.03125 mol |
| Pd(OAc)$_2$ | 0.0001 mol |
| p-toluene sulphonic acid | 0.01 mol |
| LiI | 0.01 mol |
| H$_2$O | 1 ml |
| Methyl ethyl ketone | 21 ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 10 hours continuously. The reactor was then cooled to room temperature and the gas was vented off. The contents were analysed by gas chromatography. The results of the gas chromatography showed 94% conversion of methanol with 65% selectivity to acetic acid and 4% selectivity to methyl acetate with turn over frequency (TOF) of $24h^{-1}$.

EXAMPLE 2

A 50 ml autoclave was charged with the following:

| | |
|---|---|
| Methanol | 0.03125 mol |
| Pd(OAc)$_2$ | 0.0001 mol |
| p-toluene sulphonic acid | 0.01 mol |
| NaI | 0.01 mol |
| H$_2$O | 1 ml |
| Methyl ethyl ketone | 21 ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 10 hours continuously. The reactor was then cooled to room temperature and the gas was vented off. The contents were analysed by gas chromatography. The results of the gas chromatography showed 97% conversion of methanol with 79% selectivity to acetic acid and 5% selectivity to methyl acetate with turn over frequency (TOF) of $25h^{-1}$.

EXAMPLE 3

A 50 ml autoclave was charged with the following:

| | |
|---|---|
| Methanol | 0.03125 mol |
| Pd(OAc)$_2$ | 0.0001 mol |
| p-toluene sulphonic acid | 0.01 mol |
| KI | 0.01 mol |
| H$_2$O | 1 ml |
| Methyl ethyl ketone | 21 ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 4.5 hours continuously. The reactor was then cooled to room temperature and the gas was vented off The contents were analysed by gas chromatography. The results of the gas chromatography showed 97% conversion of methanol with 74% selectivity to acetic acid and 3% selectivity to methyl acetate with turn over frequency (TOF) of $21h^{-1}$.

EXAMPLE 4

A 50 ml autoclave was charged with the following:

| | |
|---|---|
| Methanol | 0.03125 mol |
| Pd(OAc)$_2$ | 0.0001 mol |
| p-toluene sulphonic acid | 0.01 mol |
| KI | 0.01 mol |
| H$_2$O | 5 ml |
| Methyl ethyl ketone | 16 ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 4.5 hours continuously. The reactor was then cooled to room temperature and the gas was vented off. The contents were analysed by gas chromatography. The results of the gas chromatography showed 94% conversion of methanol with 65% selectivity to acetic acid and 4% selectivity to methyl acetate with turn over frequency (TOF) of $51h^{-1}$.

EXAMPLE 5

A 50 ml autoclave was charged with the following:

| | |
|---|---|
| Methanol | 0.03125 mol |
| Pd(OAc)$_2$ | 0.0001 mol |
| p-toluene sulphonic acid | 0.01 mol |
| CH$_3$I | 0.01 mol |
| H$_2$O | 1 ml |
| Methyl ethyl ketone | 21 ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 10 hours continuously. The reactor was then cooled to room temperature and the gas was vented off. The contents were analysed by gas chromatography. The results of the gas chromatography showed 23% conversion of methanol with 44% selectivity to acetic acid and 44% selectivity to methyl acetate with turn over frequency (TOF) of $3h^{-1}$.

EXAMPLE 6

A 50 ml autoclave was charged with the following:

| | |
|---|---|
| Methanol | 0.03125 mol |
| Pd(OAc)$_2$ | 0.0001 mol |
| Benzene sulphonic acid | 0.01 mol |
| LiI | 0.01 mol |
| H$_2$O | 1 ml |
| Methyl ethyl ketone | 21 ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 10 hours continuously. The reactor was then cooled to room temperature and the gas was vented off. The contents were analysed by gas chromatography. The results of the gas chromatography showed 59% conversion of methanol with 8% selectivity to acetic acid and 8% selectivity to methyl acetate with turn over frequency (TOF) of $2h^{-1}$.

EXAMPLE 7

A 50 ml autoclave was charged with the following:

| | | |
|---|---|---|
| Ethanol | 0.03125 | mol |
| Pd(OAc)$_2$ | 0.0001 | mol |
| p-toluene sulphonic acid | 0.01 | mol |
| LiI | 0.01 | mol |
| H$_2$O | 1 | ml |
| Methyl ethyl ketone | 21 | ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 10 hours continuously. The reactor was then cooled to room temperature and the gas was vented off. The contents were analysed by gas chromatography. The results of the gas chromatography showed 54% conversion of ethanol with 15% selectivity to propionic acid and 6% selectivity to ethyl propionate with turn over frequency (TOF) of $3h^{-1}$.

EXAMPLE 8

A 50 ml autoclave was charged with the following:

| | | |
|---|---|---|
| Methanol | 0.03125 | mol |
| Pd(OAc)$_2$ | 0.0001 | mol |
| p-toluene sulphonic acid | 0.01 | mol |
| LiI | 0.01 | mol |
| H$_2$O | 1 | ml |
| Acetonitrile | 21 | ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 10 hours continuously. The reactor was then cooled to room temperature and the gas was vented off The contents were analysed by gas chromatography. The results of the gas chromatography showed 83% conversion of methanol with 67% selectivity to acetic acid and 18% selectivity to methyl acetate with turn over frequency (TOF) of $16h^{-1}$.

EXAMPLE 9

A 50 ml autoclave was charged with the following:

| | | |
|---|---|---|
| Methanol | 0.03125 | mol |
| Pd(OAc)$_2$ | 0.0001 | mol |
| p-toluene sulphonic acid | 0.01 | mol |

-continued

| | | |
|---|---|---|
| HI | 0.01 | mol |
| H$_2$O | 3.8 | ml |
| Methyl ethyl ketone | 16 | ml |

The contents of the autoclave were flushed once with nitrogen and thrice with carbon monoxide at room temperature. Thereafter, the contents were heated at 115° C. The autoclave was pressurized with carbon monoxide to 800 psig after the temperature was attained. The contents were stirred for 4.5 hours continuously. The reactor was then cooled to room temperature and the gas was vented off. The contents were analysed by gas chromatography. The results of the gas chromatography showed 88% conversion of methanol with 92% selectivity to acetic acid and 2% selectivity to methyl acetate with turn over frequency (TOF) of $46h^{-1}$.

When Examples 1, 2, and 3 were repeated in the absence of organic sulphonic acid, no acetic acid or methyl acetate was formed. This clearly establishes that metal iodide and organic sulphonic acid work together for the carbonylation of methanol. The novelty in this invention lies inter alia, in the use of a catalyst system comprising palladium catalyst, and a promoter comprising organic or inorganic halide and an organic sulphonic acid for the carbonylation of an alcohol to the corresponding carboxylic acid.

Advantages of the Invention

1. The process of the invention uses an alternative catalytic system that is more economical and efficient.
2. The process can also be used for other carboxylic acids and esters other than acetic acid and methyl acetate.
3. The reaction conditions required for performance are mild.

We claim:

1. A process for the preparation of a carboxylic acid comprising carbonylating the corresponding alcohol in carbon monoxide atmosphere and in the presence of water, a solvent, a palladium catalyst and a promoter system consisting of an organic or inorganic halide and an organic sulphonic acid, at a temperature in the range of 50–250° C., at a pressure in the range of 50–2000 psig for 1 to 10 hours, the concentration of the catalyst being one mole of catalyst per every 50–50000 moles of the alcohol, the amount of the organic or inorganic halide being in the range of 5–500 moles per mole of the catalyst, and the amount of the organic sulphonic acid being in the range of 5–500 moles per mole of the catalyst, collecting the resulting product.

2. A process as claimed in claim 1 wherein the alcohol used is ROH wherein R is an alkyl group having 1 to 5 carbon atoms.

3. A process as claimed in claim 1 wherein the catalyst used comprises a palladium (II) or palladium (0) compound selected from the group consisting of palladium chloride, palladium bromide, palladium iodide and palladium acetate; or a metal complex of palladium selected from the group consisting of bis(triphenylphosphino) dichloropalladium (II), bis(triphenylphosphino)bibromopalladium (II), bis(triparatolylphosphino)dichloropalladium (II), bis(triparatolylphosphino)bibromopalladium (II), tetrakis (triphenylphosphino)dichloropalladium (0) and tetrakis (triphenylphosphino) dibromopalladium (0).

4. A process as claimed in claim 1 wherein the organic halide used is of the formula RX wherein R is an alkyl group having 1 to 5 carbon atoms and X is a halogen selected from Cl, Br, and I.

5. A process as claimed in claim 1 wherein the inorganic halide used is of the formula MX wherein M is hydrogen or an alkali metal selected from the group consisting of Li, Na and K, and X is a halogen selected from Cl, Br and I.

6. A process as claimed in claim 1 wherein the organic sulphonic acid used is selected from the group consisting of benzene sulphonic acid, paratolyl sulphonic acid, methane sulphonic acid, and trifluoromethane sulphonic acid.

7. A process as claimed in claim 1 wherein the solvent used comprises a ketone selected from the group consisting of acetone, diethyl ketone and acetophenone; or a cyclic ether selected from tetrahydrofuran and dioxan; or a nitrile selected from acetonitrile and benzonitrile; or an organic solvent selected from toluene and benzene.

8. A process as claimed in claim 1 wherein the concentration of the catalyst is one mole of catalyst for every 100–5000 moles of the alcohol.

9. A process as claimed in claim 8 wherein the concentration of the catalyst is one mole of catalyst for every 150–1000 moles of the alcohol.

10. A process as claimed in claim 1 wherein the amount of organic or inorganic halide promoter used is in the range of 25 to 150 moles per mole of catalyst.

11. A process as claimed in claim 1 wherein the amount of the organic sulphonic acid used is in the range of 50–150 moles per mole of catalyst.

12. A process as claimed in claim 1 wherein the amount of water is in the range of 1 to 30%(v/v) of the total reaction mixture.

13. A process as claimed in claim 12 wherein the amount of water is in the range of 3–25%(v/v) of the total reaction mixture.

14. A process as claimed in claim 1 wherein the pressure of the carbon monoxide used is in the range of 200–1000 psig.

15. A process as claimed in claim 1 wherein the temperature of the reaction mixture is in the range of 70–200° C.

\* \* \* \* \*